(12) United States Patent
Austen, Jr. et al.

(10) Patent No.: US 11,337,792 B2
(45) Date of Patent: May 24, 2022

(54) METHODS FOR TISSUE PASSIVATION

(71) Applicant: The General Hospital Corporation, Boston, MA (US)

(72) Inventors: William G. Austen, Jr., Weston, MA (US); Michael McCormack, Medford, MA (US); Robert W. Redmond, Lancaster, MA (US); Irene E. Kochevar, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 53 days.

(21) Appl. No.: 16/686,691

(22) Filed: Nov. 18, 2019

(65) Prior Publication Data

US 2020/0078159 A1 Mar. 12, 2020

Related U.S. Application Data

(60) Division of application No. 14/601,023, filed on Jan. 20, 2015, now Pat. No. 10,478,284, which is a
(Continued)

(51) Int. Cl.
*A61F 2/06* (2013.01)
*A61K 41/00* (2020.01)
(Continued)

(52) U.S. Cl.
CPC ............ *A61F 2/06* (2013.01); *A61K 41/0057* (2013.01); *A61L 27/3604* (2013.01); *A61L 27/3633* (2013.01); *A61L 27/50* (2013.01); *A61L 27/505* (2013.01); *A61L 27/54* (2013.01); *A61L 31/005* (2013.01); *A61L 31/14* (2013.01);
(Continued)

(58) Field of Classification Search
CPC ...... A61F 2/06–2/062; A61F 2002/068; A61F 2210/00; A61F 2240/00–2240/001; A61F 2250/0057; A61K 41/0057; A61K 2300/00; A61L 27/3604; A61L 27/3633; A61L 27/50; A61L 27/505; A61L 27/54; A61L 31/005; A61L 31/14; A61L 31/16; A61L 2300/418; A61L 2300/424; A61L 2400/18; A61L 2430/04; A61L 2430/22; A61L 2430/34; A61N 5/0603; A61N 5/0624; A61N 5/0601; A61N 5/062
See application file for complete search history.

(56) References Cited

U.S. PATENT DOCUMENTS 7,037,490 B2 * 5/2006 Rowe ................. A61B 1/00165
424/426
2002/0187935 A1 * 12/2002 Redmond ............... A61L 27/50
514/100

(Continued)

*Primary Examiner* — Paul B Prebilic
(74) *Attorney, Agent, or Firm* — Quarles & Brady LLP

(57) ABSTRACT

One aspect of the invention provides a method of preventing or reducing stenosis in a subject. The method includes implanting a passivated graft comprising vein into an artery. The implanting of the graft replaces and/or bypasses a diseased segment of the artery. The passivated graft including vein is prepared by exposing the exterior surface of the passivated graft comprising vein to a tissue structure stabilizing agent ("TSSA") under conditions sufficient to promote cross-linking of proteins within the vein.

7 Claims, 9 Drawing Sheets

Related U.S. Application Data continuation-in-part of application No. PCT/US2013/051333, filed on Jul. 19, 2013.

(60) Provisional application No. 61/847,794, filed on Jul. 18, 2013, provisional application No. 61/784,708, filed on Mar. 14, 2013, provisional application No. 61/674,235, filed on Jul. 20, 2012.

(51) Int. Cl.
| | | |
|---|---|---|
| *A61L 27/36* | (2006.01) | |
| *A61N 5/06* | (2006.01) | |
| *A61L 27/50* | (2006.01) | |
| *A61L 27/54* | (2006.01) | |
| *A61L 31/00* | (2006.01) | |
| *A61L 31/14* | (2006.01) | |
| *A61L 31/16* | (2006.01) | |

(52) U.S. Cl.
CPC .......... *A61L 31/16* (2013.01); *A61N 5/0601* (2013.01); *A61N 5/062* (2013.01); *A61L 2300/418* (2013.01); *A61L 2300/424* (2013.01); *A61L 2300/442* (2013.01); *A61L 2400/18* (2013.01); *A61L 2430/04* (2013.01); *A61L 2430/22* (2013.01); *A61L 2430/34* (2013.01); *A61N 5/0603* (2013.01); *A61N 5/0624* (2013.01)

(56) References Cited

U.S. PATENT DOCUMENTS

| | | | | |
|---|---|---|---|---|
| 2003/0100934 | A1* | 5/2003 | Stephens | A61N 5/062 607/88 |
| 2004/0208855 | A1* | 10/2004 | Allison | A61K 41/0057 424/93.7 |
| 2005/0113288 | A1* | 5/2005 | Utecht | A61K 41/0042 514/55 |
| 2006/0212070 | A1* | 9/2006 | Redmond | A61F 9/008 606/214 |
| 2012/0209051 | A1* | 8/2012 | Blumenkranz | A61P 27/02 600/2 |

* cited by examiner

Vascular Access

METHODS FOR TISSUE PASSIVATION

CROSS-REFERENCE TO RELATED APPLICATIONS

This application is a divisional of U.S. patent application Ser. No. 14/601,023, filed Jan. 20, 2015 and issued as U.S. Pat. No. 10,478,284 on Nov. 19, 2019, which is continuation-in-part of International Application No. PCT/US2013/051333, filed on Jul. 19, 2013 and published in English as WO 2014/015274 on Jan. 23, 2014, which claims the benefit of U.S. provisional application Ser. No. 61/674,235, filed on Jul. 20, 2012, 61/784,708, filed on Mar. 14, 2013 and 61/847,794, filed on Jul. 18, 2013. The entire disclosure of each of the aforementioned patent applications is incorporated herein by reference.

BACKGROUND OF THE INVENTION

Capsular contracture is one of the most common causes of reoperation following implantation[3,6]. The etiology of capsular contracture has been studied for many years[3]. Potential etiologies include hematoma, hypertrophic scar and, microbacterial infections caused by *Staphylococcus epidermidis*[7-9]. Regardless of the etiology, the end result is an inflammatory response within the implant pocket and near the developing capsule[2,10].

Neocollagen formation and cross-linking are part of the normal human wound healing response. In capsular contracture, these processes go awry, resulting in dense, linear bundles of collagen fibers that surround the affected implant. These fibers form a firm capsule that subsequently contracts and tightens[11]. Histologically, this appears as an inner layer of fibroblasts and histiocytes that is surrounded by a thicker layer of collagen bundles arranged in a parallel array[2,12]. Direct pressure from a maturing capsule may deform or rupture the implant, in addition to distorting the overlying skin and soft tissue.

Capsular contracture is the most common complication following augmentation mammoplasty with prosthetic implants. Within a decade of surgery, half of the patients may develop capsular contracture and nearly a quarter develops severe disease[1]. The condition may be painful and debilitating as well as aesthetically inferior. Despite decades of research, effective methods of prevention of capsular contracture remain elusive[3]. Surgical capsulotomy and/or capsulectomy are, to date, the gold standard treatments for affected patients but neither offers protection from recurrent disease[4-5]. Therefore, methods to prevent the initial incidence of capsular contracture as well as its recurrence would be highly desirable.

Saphenous vein grafts (SVGs) used for coronary artery bypass graft (CABG) have poor long-term patency rates compared to arterial grafts. In fact, 20% of SVGs fail within one year of CABG and 50% fail within ten years. Of the vein grafts that remaining patent, 50% have a significant atherosclerotic burden. Veins grafts for peripheral arterial reconstruction and Arteriovenous fistula (AVF) for vascular access suffer from similar shortcomings.

The poor long-term outcomes are due to the luminal narrowing resulting from intimal hyperplasia, medial thickening and subsequent superimposed accelerated atherosclerosis. Intimal hyperplasia is a consequence of the intimal injury that ensues after excessive dilation of the vein graft as it is exposed to arterial pressures.

One solution to prevent over-distention is providing external mechanical support, which has been shown to reduce the degree of intimal hyperplasia in humans. To date, every form of mechanical support involves the use of external sheaths, which are applied over the vein graft prior to implantation and exposure to arterial pressure. External sheaths are cumbersome to use and can lead to technical difficulties. Furthermore, there is a risk of erosion and/or infection because it is a foreign body. A non-external mechanical support solution to reduce the degree of intimal injury caused by tissue expansion of venous grafts when they are exposed to arterial pressure would also be highly desirable.

SUMMARY OF THE INVENTION

The recitation of an embodiment below includes that embodiment as any single embodiment or in combination with any other embodiments or portions thereof and the recited embodiments are applicable to one or more of the aspects recited below.

In one aspect, the invention provides a method of preparing a non-adhesive tissue surface within a human subject, the method comprising the step of exposing an intact, non-proliferative, internal tissue surface located proximal to an incision in a human subject to a tissue structure stabilizing agent ("TSSA") under conditions sufficient to promote cross-linking of proteins within the surface of the tissue, thereby preparing a non-adhesive tissue surface within the human subject.

In one embodiment, the tissue surface is located within a cavity of the human subject. In another embodiment, the tissue surface is within a tissue selected from the group consisting of connective, epithelial, muscle, nervous, circulatory (e.g., veins, arteries, valves etc.), abdominal, bladder, bowel, thoracic, colorectal, rectal, intestinal, ovarian, uterine, pericardial, peritoneal, oral, cardiac (e.g., endocardial) and breast tissue. In yet another embodiment, the tissue surface comprises previously grafted tissue.

In a further embodiment, the TSSA is applied topically to the tissue surface. In another embodiment, the tissue surface has an area of about 20 $cm^2$, 25 $cm^2$, 50 $cm^2$, 100 $cm^2$, 500 $cm^2$ to about 1000 $cm^2$.

In one embodiment, the TSSA is a photoactive agent or a chemical cross-linking compound.

In certain embodiments, the TSSA is a photoactive agent. In one embodiment, the method further comprises the step of irradiating the tissue surface at an irradiance of less than about 1 $W/cm^2$. In one embodiment, the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In another embodiment, the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof. In certain embodiments, the photoactive agent is RB.

In one embodiment, the irradiance is provided for a period between about 1 minute and 30 minutes. In another embodiment, the irradiance is provided for less than about 5 minutes.

In yet another embodiment, the method further comprises providing an implant to the human subject following irradiation and closing the incision. In certain embodiments, the method further comprises providing an implant to the human subject containing a light source for irradiating the tissue surface.

In one embodiment, the TSSA is chemical cross-linking compound. In one embodiment, the chemical cross-linking compound is selected from the group consisting of dimethyl suberimidate, N-Hydroxysuccinimide-ester cross-linker BS3, formaldehyde, 1-ethyl-3-(3-dimethylaminopropyl)-carbodiimide ("EDC") and methyl (2R,2R,6S)-2-hydroxy-9-(hydroxymethyl)-3-oxabicyclo[4.3.0]nona-4,8-diene-5-carboxylate) ("Genipin"). In certain embodiments, the chemical cross-linking compound is 1-ethyl-3-(3-dimethylaminopropyl)-carbodiimide ("EDC") or methyl (2R,2R,6S)-2-hydroxy-9-(hydroxymethyl)-3-oxabicyclo[4.3.0]nona-4,8-diene-5-carboxylate) ("Genipin"). In certain other embodiments, the chemical cross-linking compound is EDC.

In another aspect, the invention provides a method of preventing or decreasing tissue adhesion and/or contracture at a surgical site in a human subject, the method comprising the steps of: topically applying a tissue structure stabilizing agent ("TSSA") to an internal tissue surface proximally located to a surgical site under conditions sufficient to promote cross-linking of proteins within the surface of the tissue; and determining that tissue adhesion and/or contracture at the surgical site is decreased compared to a reference, thereby preventing or decreasing tissue adhesion and/or contracture at a surgical site in human subject.

In one embodiment, the contracture comprises scar contracture or capsular contracture.

In another embodiment, the TSSA is a photoactive agent or a chemical cross-linking compound.

In yet another embodiment, the TSSA is a photoactive agent. In one embodiment, the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In another embodiment, the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof. In certain embodiments, the photoactive agent is RB.

In still another embodiment, the TSSA is a chemical cross-linking compound. In one embodiment, the chemical cross-linking compound is selected from the group consisting of dimethyl suberimidate, N-Hydroxysuccinimide-ester cross-linker BS3, formaldehyde, 1-ethyl-3-(3-dimethylaminopropyl)-carbodiimide ("EDC") and methyl (2R,2R,6S)-2-hydroxy-9-(hydroxymethyl)-3-oxabicyclo[4.3.0]nona-4,8-diene-5-carboxylate) ("Genipin"). In certain embodiments, the chemical cross-linking compound is 1-ethyl-3-(3-dimethylaminopropyl)-carbodiimide ("EDC") or methyl (2R,2R,6S)-2-hydroxy-9-(hydroxymethyl)-3-oxabicyclo[4.3.0]nona-4,8-diene-5-carboxylate) ("Genipin"). In certain other embodiments, the chemical cross-linking compound is EDC.

In yet another aspect, the invention provides a method of preparing a non-adhesive tissue surface within a human subject, the method comprising the steps of: topically applying a photoactive agent to an internal tissue surface within a cavity, wherein the surface is about 20 $cm^2$, 25 $cm^2$, 50 $cm^2$, 100 $cm^2$, 500 $cm^2$ to about 1000 $cm^2$, and irradiating the tissue surface at an irradiance of less than about 1 $W/cm^2$, thereby preparing a non-adhesive tissue surface within the human subject.

In one embodiment, the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In another embodiment, the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof. In certain embodiments, the photoactive agent is RB.

In certain embodiments, the irradiance is provided for a period between about 1 minute and 30 minutes. In other embodiments, the irradiance is provided for less than about 5 minutes. In another embodiment, the tissue surface is located within a cavity of the human subject.

In yet another embodiment, the tissue surface is within a tissue selected from the group consisting of connective, epithelial, muscle, nervous, circulatory, abdominal, bladder, bowel, thoracic, colorectal, rectal, intestinal, ovarian, uterine, pericardial, peritoneal, oral, cardiac (e.g., endocardial) and breast tissue.

In still another embodiment, the tissue surface comprises previously grafted tissue.

In one embodiment, the photoactive agent is applied topically to the tissue surface.

In another embodiment, methods of the invention further comprise providing an implant to the human subject following irradiation and closing the incision.

In yet another embodiment, methods of the invention further comprise providing an implant to the human subject containing a light source for irradiating the tissue surface.

Another aspect of the invention provides a method of preparing a tissue for therapeutic use, the method comprising the step of exposing the external surface of a tissue to a tissue structure stabilizing agent ("TSSA") under conditions sufficient to promote cross-linking of proteins within the surface of the tissue, thereby preparing a tissue for therapeutic use.

In one embodiment, the external surface of the tissue is exposed to the TSSA, e.g., ex vivo.

In another embodiment, the tissue is a tissue graft or arteriovenous fistula "(AVF").

In one embodiment, the tissue is a tissue graft. In another embodiment, the tissue graft is prepared for implantation in a subject. In yet another embodiment, the tissue graft comprises a tissue selected from the group consisting of circulatory (e.g., vein, artery, capillary, valve, etc.), connective, bone, ligament, tendon, skin, muscle and cardiac tissue (e.g., arteries, veins, ventricles, coronary valves, etc.). In still another embodiment, the tissue graft comprises vein.

In one embodiment, the tissue is an AVF. In another embodiment, the AVF is prepared for therapeutic use for venous access. In one embodiment, the AVF comprises vein. In another embodiment, the AVF comprises an arteriovenous graft ("AVG").

In one embodiment, the tissue comprises a member selected from the group consisting of autologous tissue, extracellular matrix tissue and tissue substitute. In another embodiment, the extracellular matrix comprises collagen or proteoglycan. In yet another embodiment, the tissue substitute comprises a member selected from the group consisting of silicone, collagen, fibronectin, glycosaminoglycan, polyurethane, polyvinyl and nylon.

In one embodiment, the TSSA is provided to the external surface of the tissue.

In one embodiment, the TSSA is a photoactive agent or a chemical cross-linking compound.

In one embodiment, the TSSA is a photoactive agent. In certain embodiments, the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In another embodiment, the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof.

In certain embodiments, the photoactive agent is RB.

In one embodiment, the chemical cross-linking compound is selected from the group consisting of dimethyl suberimidate, N-Hydroxysuccinimide-ester cross-linker BS3, formaldehyde, 1-ethyl-3-(3-dimethylaminopropyl)-carbodiimide ("EDC") and methyl (2R,2R,6S)-2-hydroxy-9-(hydroxymethyl)-3-oxabicyclo[4.3.0]nona-4,8-diene-5-carboxylate) ("Genipin"). In certain embodiments, the chemical cross-linking compound is 1-ethyl-3-(3-dimethylaminopropyl)-carbodiimide ("EDC") or methyl (2R,2R,6S)-2-hydroxy-9-(hydroxymethyl)-3-oxabicyclo[4.3.0]nona-4,8-diene-5-carboxylate) ("Genipin"). In certain other embodiments, the chemical cross-linking compound is EDC.

Another aspect of the invention provides a method of preparing a tissue for therapeutic use, the method comprising the steps of: providing Rose Bengal to the external surface of a tissue and irradiating the surface at an irradiance of less than about 1 W/cm², thereby preparing a tissue for therapeutic use. In one embodiment, the tissue comprises a tissue graft.

In yet another aspect, the invention provides a method of preparing a vein for therapeutic use, the method comprising exposing the external surface of the vein to a tissue structure stabilizing agent ("TSSA") under conditions sufficient to promote cross-linking of proteins within the vein, thereby preparing the vein for therapeutic use.

In one embodiment, the TSSA is a photoactive agent or a chemical cross-linking compound.

In one embodiment, the TSSA is a photoactive agent. In certain embodiments, the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In another embodiment, the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof.

In certain embodiments, the photoactive agent is RB.

In another embodiment, the TSSA is a chemical cross-linking compound. In one embodiment, the chemical cross-linking compound is selected from the group consisting of dimethyl suberimidate, N-Hydroxysuccinimide-ester cross-linker BS3, formaldehyde, 1-ethyl-3-(3-dimethylaminopropyl)-carbodiimide ("EDC") and methyl (2R,2R,6S)-2-hydroxy-9-(hydroxymethyl)-3-oxabicyclo[4.3.0]nona-4,8-diene-5-carboxylate) ("Genipin"). In certain embodiments, the chemical cross-linking compound is 1-ethyl-3-(3-dimethylaminopropyl)-carbodiimide ("EDC") or methyl (2R,2R,6S)-2-hydroxy-9-(hydroxymethyl)-3-oxabicyclo[4.3.0]nona-4,8-diene-5-carboxylate) ("Genipin"). In certain other embodiments, the chemical cross-linking compound is EDC.

In still another aspect, the invention provides a method of preparing an external surface of a graft comprising vein or AVF comprising vein for therapeutic use, the method comprising the steps of: providing Rose Bengal to the graft comprising vein or the AVF comprising vein; and irradiating the graft or the AVF at an irradiance of less than about 1 W/cm², thereby preparing the graft comprising vein or AVF comprising vein for therapeutic use.

In one embodiment, the graft comprising vein is prepared for implantation.

In another embodiment, the AVF comprising vein is prepared for venous access. In certain embodiments, the AVF comprising vein is prepared for venous access for use in hemodialysis in a subject with severe kidney disease In yet another aspect, the invention provides a method of preventing or reducing stenosis in a subject, the method comprising the step of implanting a passivated graft comprising vein into an artery, wherein the implanting of the graft replaces and/or bypasses a diseased segment of the artery, thereby preventing or reducing stenosis in a subject.

In one embodiment, the passivated graft is prepared by exposing the exterior surface of the graft comprising vein to a tissue structure stabilizing agent ("TSSA") under conditions sufficient to promote cross-linking of proteins within the graft.

In another embodiment, the method further comprises exposing the exterior surface of the implanted, passivated graft comprising vein and/or the exterior surface of the artery to a TSSA under conditions sufficient to promote cross-linking of proteins within exterior surface.

In one embodiment, the diseased segment of the artery contains a plaque.

In one embodiment, the TSSA is a photoactive agent or a chemical cross-linking compound.

In one embodiment, the TSSA is a photoactive agent. In certain embodiments, the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes. In another embodiment, the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof. In certain embodiments, the photoactive agent is RB. In yet another embodiment, Rose Bengal is provided to the exterior surface of the implanted, passivated graft or arteriovenous fistula comprising vein and/or the exterior surface of the artery and irradiated at an irradiance of less than about 1 W/cm².

In another embodiment, the TSSA is a chemical cross-linking compound. In one embodiment, the chemical cross-linking compound is selected from the group consisting of dimethyl suberimidate, N-Hydroxysuccinimide-ester cross-linker BS3, formaldehyde, 1-ethyl-3-(3-dimethylaminopropyl)-carbodiimide ("EDC") and methyl (2R,2R,6S)-2-hydroxy-9-(hydroxymethyl)-3-oxabicyclo[4.3.0]nona-4,8-diene-5-carboxylate) ("Genipin"). In certain embodiments, the chemical cross-linking compound is 1-ethyl-3-(3-dimethylaminopropyl)-carbodiimide ("EDC") or methyl (2R, 2R,6S)-2-hydroxy-9-(hydroxymethyl)-3-oxabicyclo[4.3.0] nona-4,8-diene-5-carboxylate) ("Genipin"). In certain other embodiments, the chemical cross-linking compound is EDC.

In yet another aspect, the invention provides a method of preventing or reducing stenosis in a subject, the method comprising the steps of: implanting a graft comprising vein into an artery, wherein the implanting of the graft replaces and or bypasses a diseased segment of the artery, providing Rose Bengal to the exterior surface of the implanted graft comprising vein and irradiating the graft at an irradiance of less than about 1 W/cm$^2$, thereby preventing or reducing stenosis in a subject.

Other features and advantages of the invention will be apparent from the detailed description and from the claims. Thus, other aspects and embodiments of the invention are described in the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

DETAILED DESCRIPTION OF THE INVENTION

Definitions

Figure 1:
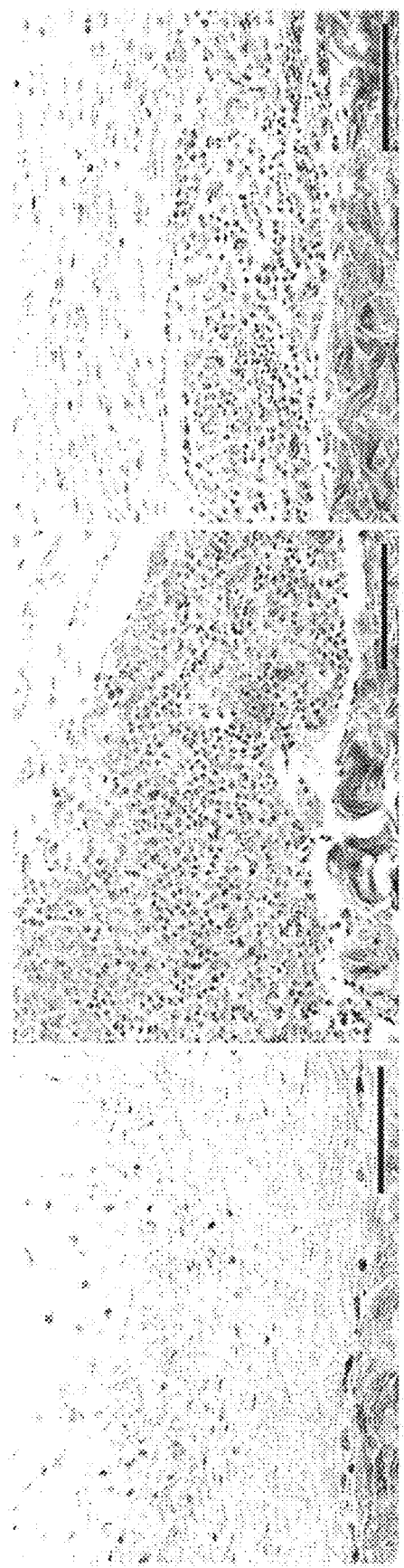
FIG. 1 depicts tissue harvested at two weeks, stained with mason's trichrome. Pockets that received no fibrin glue (left), fibrin glue (center), fibrin glue and pretreatment with PTP (right) are shown. (Scale Bar=100 µm).

Unless otherwise defined, all technical and scientific terms used herein have the same meaning as commonly understood by one of ordinary skill in the art to which this invention pertains. In case of conflict, the present application, including definitions, will control.

The term "tissue structure stabilizing agent" ("TSSA)" refers to an agent that promotes mechanically strengthened tissue structures, such as, e.g., veins, arteries, grafts, etc., via cross-linking among and/or between proteins naturally present in tissue. TSSAs include photoactive agents and chemical cross-linking compounds.

The term "intact tissue" as used herein refers to tissue that is uninjured, continuous and/or whole (e.g., refers to tissue that has not been severed, separated or wounded). Intact tissue may be homogenous or alternatively, may comprise a mixture of native and previously grafted tissue that has become a continuous tissue as a result of grafting.

The term "non-proliferative tissue" as used herein refers to a state or condition of normal cell growth (e.g., refers to a state or condition that is not characterized by, for example, rapidly proliferating cell growth, such as in cancer or atherosclerosis).

The term "internal tissue" as used herein refers to an anatomical site located within the body (e.g., a body cavity, connective tissue or internal organ system) and not located on the external surface of the body (e.g., the term does not include external tissues, such as skin and cornea).

The term "proximally located to an incision" as used herein refers to an internal anatomical site surrounding, or adjacent to, an incision but not including the incision.

The term "arteriovenous fistula (AVF)" refers to a certain type of connection between an artery and a vein. Normally, blood flows from arteries to capillaries to veins. Nutrients and oxygen in the blood travel from capillaries to tissues in the body. With an abnormal AVF, blood flows directly from an artery into a vein, bypassing some capillaries and thereby depriving capillaries and associated tissues of blood flow. AVFs can develop anywhere in the body but often occur in the legs. AVFs may be artificially created to aid in treatment of various conditions, e.g., by providing venous access, e.g., for use in hemodialysis in people with severe kidney disease. In this regard, the term AVF can comprise a natural tissue, e.g., vein, or a tissue substitute, e.g., an artificial material.

When the AVF comprises an artificial material, it is referred to as an arteriovenous graft ("AVG").

The term "passivated tissue" as used herein refers to a tissue that has been treated with a TSSA.

The term "passivated tissue graft" as used herein refers to a tissue graft treated with a TSSA. Grafts thus passivated may be implanted into a subject, e.g., to prevent or reduce stenosis in the subject.

The term "passivated arteriovenous fistula (AVF)" as used herein refers to an AVF that has been treated with a TSSA. The thus treated AVF can be subsequently connected to an artery in a subject, thereby creating the fistula in a subject. The passivated AVF can be used for vascular access, e.g., for use in hemodialysis in people with severe kidney disease.

The term "circulatory tissue" as used herein refers to any tissue associated with the blood circulatory system in the body, e.g., veins, arteries, capillaries, valves, etc.

The term "cardiac tissue" as used herein refers to any tissue associated with the heart, e.g., arteries, veins, valves, ventricles, cardiac muscle, etc.

The term "muscle" as used herein refers to any muscle in the body other than cardiac muscle.

The term "non-adhesive tissue surface" as used herein refers to a tissue surface containing a reduced amount of pathogenic collagen bundles and/or capsular contracture compared to a reference standard.

The term "therapeutic use" as used herein refers to any procedure, protocol or regimen intended to treat, prevent and/or cure an abnormal health condition, disease or symptom(s) thereof.

The term "reduce" or "decrease" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. substantially absent or below levels of detection), or any decrease between 10-100% as compared to a reference level, as that term is defined herein.

As used herein, the term "standard" or "reference" can simply be a reference that defines a baseline for comparison, such as an amount or level of adhesion, capsular contracture and/or pathogenic collagen bundle formation known to occur in the absence of photochemical or chemical tissue passivation.

A "subject" is a vertebrate, including any member of the class mammalia, including humans, domestic and farm animals, and zoo, sports or pet animals, such as mouse, rabbit, pig, sheep, goat, cattle and higher primates.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The recitation of a listing of elements in any definition of a variable herein includes definitions of that variable as any single element or combination (or sub combination) of listed elements.

Other definitions appear in context throughout this disclosure.

Methods of the Invention

It has now been determined that treating a tissue surface with an appropriate TSSA, e.g., a photoactive agent and light or a chemical cross-linking compound, intra-surgically, can create a less reactive tissue surface with normal tissue architecture and reduced post-surgical inflammation, which prevents the development of pathogenic collagen bundles (i.e., fibrotic response) following surgery. This approach, referred to as Tissue Passivation, leads to reduced adhesion formation, scarring and wound contracture as a result of reducing tissue surface reactivity. Clinical applications for Tissue Passivation include, but are not limited to, scar contracture, capsular contracture around implants, inhibition of intra-abdominal adhesions after abdominal, thoracic, chest, colorectal, and ovarian surgery, inhibition of adhesions following uterine, fibroid resection, treatment of irradiate breast tissue, pretreatment of vein to prevent stenosis, treatment of vascular grant post angioplasty to prevent stenosis, treatment of arteriovenous fistula for vascular access to prevent stenosis, host tissue preparation for knee and hip replacements, ligament surgeries and treatment for cellulitis.

Cross-Linking

Proteins naturally present in the body can contain cross-links generated by enzyme-catalyzed or spontaneous reactions. Such cross-links are important in generating mechanically stable tissue structures such as hair, skin and cartilage. Disulfide bond formation is one of the most common types of cross-linking but isopeptide bond formation is also common. Proteins can also be cross-linked artificially, e.g., chemically cross-linked, using photoactive agents/photo activation and chemical cross-linking agents ("PTP"). Cross-linking strengthens, e.g., veins and arteries, by altering tissue compliance and thereby limiting tissue expansion in all directions, i.e., limiting tissue dilatation and lengthening.

Photoactivation and Photoactive Agents

Photoactivation, as referred to herein, e.g., can be used to describe the process by which energy in the form of electromagnetic radiation is absorbed by a compound, e.g., a photoactive agent, thus "exciting" the compound, which then becomes capable of converting the energy to another form of energy, preferably chemical energy. The electromagnetic radiation can include energy, e.g., light, having a wavelength in the visible range or portion of the electromagnetic spectrum, or the ultra violet and infrared regions of the spectrum. The chemical energy can be in the form of a reactive species, e.g., a reactive oxygen species, e.g., a singlet oxygen, superoxide anion, hydroxyl radical, the excited state of the photoactive agent, free radical or substrate free radical species. The photoactivation process can involve an insubstantial transfer of the absorbed energy into heat energy.

As used herein, a photoactive agent is a chemical compound that produces a biological effect upon photoactivation or a biological precursor of a compound that produces a biological effect upon photoactivation. Exemplary photoactive agents can be those that absorb electromagnetic energy, such as light. While not wishing to be bound by theory, the photoactivated agent may act by producing an excitation state or derived species that interacts with tissue to produce effects including protein cross-linking, modification of cell signaling pathways, oxidative stress, extracellular matrix alterations, cytokine and growth factor inhibition or release.

Certain exemplary photoactive agents typically have chemical structures that include multiple conjugated rings that allow for light absorption and photoactivation. A number of photoactive agents are known to one of skill in the art, and generally include a variety of light-sensitive dyes and biological molecules. Examples include, but are not limited to, xanthenes, e.g., Rose Bengal ("RB") and erythrosin; flavins, e.g., riboflavin; thiazines, e.g., methylene blue (MB); porphyrins and expanded porphyrins, e.g., protoporphyrin I through protoporphyrin IX, coproporphyria, uroporphyrins, mesoporphyrins, hematoporphyrins and sapphyrins; chlorophylls, e.g., bacteriochlorophyll A, phenothiazine (e.g., Toluidine Blue), cyanine, Mono azo dye (e.g., Methyl Red), Azine mono azo dye (e.g., Janus Green B), rhodamine dye (e.g., Rhodamine B base), benzophenoxazine dye (e.g., Nile Blue A, Nile Red), oxazine (e.g., Celestine Blue), anthroquinone dye (e.g., Remazol Brilliant Blue R), riboflavin-5-phosphate (R-5-P) and N-hydroxy-pyridine-2-(I H)-thione (N-HTP) and photoactive derivatives thereof.

Photoactive agents include photoactive dyes, which are organic compounds that absorb visible light resulting in a photochemical reaction. Photoactive dyes include xanthenes, thiazines, porphyrins and expanded porphyrins, chlorophylis, phenothiazines, cyanines, Mono azo dye, Azine mono azo dye, rhodamine dye, benzophenoxazine dye, oxazine, and anthroquinone dye. In certain exemplary embodiments, a photoactive agent, e.g., RB, R-5-P, MB, or N-HTP, can be dissolved in a biocompatible buffer or solution, e.g., saline solution, and used at a concentration of from about 0.1 mM to 10 mM, preferably from about 0.5 mM to 5 mM, more preferably from about 1 mM to 3 mM.

Photoactive agents can be brushed, dripped or sprayed onto, or injected into, tissue surfaces prior to the application of electromagnetic energy. The electromagnetic radiation, e.g., light, can be applied to the tissue at an appropriate wavelength, energy, and duration, to cause passivation of the tissue surface. The wavelength of light can be chosen so that it corresponds to or encompasses the absorption of the photoactive agent, and reaches the area of the tissue that has been contacted with the photoactive agent, e.g., penetrates into the region where it is applied. The electromagnetic radiation, e.g., light, necessary to achieve photoactivation of the agent can have a wavelength from about 350 nm to about 800 nm, preferably from about 400 to 700 nm and can be within the visible, infra red or near ultra violet spectra. The energy can be delivered at an irradiance of about between 0.5 and 5 W/cm$^2$, preferably between about 1 and 3 W/cm$^2$ or less than about 1 W/cm$^2$. The duration of irradiation can be brief and sufficient to allow passivation of the tissue, e.g., of a tissue collagen.

In certain exemplary embodiments, the photoactive agent applied to a tissue is a photoactive dye, e.g., RB, subject to an irradiance of less than about 1 W/cm$^2$ for a period between about 1 minute and 30 minutes. In other exemplary embodiments, the irradiance is provided for less than about 5 minutes.

Suitable sources of electromagnetic energy can include, but are not limited to, commercially available lasers, lamps, light emitting diodes, or other sources of electromagnetic radiation. Light radiation can be supplied in the form of a monochromatic laser beam, e.g., an argon laser beam or diode-pumped solid-state laser beam. Light can also be supplied to a non-external surface tissue through an optical fiber device, e.g., the light can be delivered by optical fibers threaded through a small gauge hypodermic needle or an arthroscope. Light can also be transmitted by percutaneous instrumentation using optical fibers or cannulated waveguides.

The choice of energy source can generally be made in conjunction with the choice of photoactive agent employed in the method. For example, an argon laser can be an energy source suitable for use with RB or R-5-P because these dyes are optimally excited at wavelengths corresponding to the wavelength of the radiation emitted by the argon laser.

Other suitable combinations of lasers and photosensitizers are known to those of skill in the art. Tunable dye lasers can also be used with the methods described herein.

Chemical Cross-Linking Compounds

Examples of some common chemical cross-linking compounds are the imidoester cross-linker dimethyl suberimidate, the N-Hydroxysuccinimide-ester cross-linker BS3 and formaldehyde. Each of these cross-linkers appears to induce nucleophilic attack of the amino group of lysine and subsequent covalent bonding via the cross-linker. Other examples include 1-ethyl-3-(3-dimethylaminopropyl)-carbodiimide ("EDC") and methyl (2R,2R,6S)-2-hydroxy-9-(hydroxymethyl)-3-oxabicyclo[4.3.0]nona-4,8-diene-5-carboxylate) ("Genipin").

Without being bound by theory, the zero-length carbodiimide cross-linker EDC appears to function by converting carboxyls into amine-reactive isourea intermediates that bind to lysine residues or other available primary amines. Likewise, Genipin appears to function via nucleophilic attack by a primary amine occurring at the C3 carbon atom of Genipin and secondary amine attachment to the aldehyde group of Genipin. It is believed that the protein structure is stabilized through intra/intermolecular cross-linking.

Chemical cross-linking compounds can be brushed, dripped or sprayed onto, or injected into, tissue surfaces prior.

Applications

Preparation of tissue surfaces according to passivation methods disclosed herein is useful for a variety of tissues, including but not limited to tissue surfaces within connective tissue, abdominal, bladder, bowel, thoracic, colorectal, rectal, intestinal, ovarian, uterine, pericardial, peritoneal, oral, cardiac (e.g., endocardial, epithelial and breast tissue. Passivation of body cavities prior to surgery is also envisioned. For example, body cavities having a surface area of about 20 cm$^2$, 25 cm$^2$, 50 cm$^2$, 100 cm$^2$, 500 cm$^2$ to about 1000 cm$^2$ can be treated prior to, following, or prior to and following surgical procedures, including implantation of natural or synthetic materials (e.g., breast implants). In surgical procedures not including implantation, passivation methods disclosed herein are useful for reducing reactivity of tissue surfaces which may otherwise develop adhesions and/or contracture, such as uterine-abdominal adhesions that form after caesarian sections.

Specific clinical applications also include passivation of tissue grafts and/or surgical sites to prevent contracture, scar contracture, capsular contracture around implants, inhibition of intra-abdominal adhesions after abdominal, thoracic, chest, colorectal, and ovarian surgery, inhibition of adhesions following uterine fibroid resection, treatment of radiated breast tissue, host tissue preparation for knee and hip replacements, ligament and tendon surgeries, treatment for cellulitis, treatment for hernia and treatment for dilatation.

Methods of passivation disclosed here in can be adapted for any organ in the body including but not limited to, heart, lung, cornea and nerve (e.g., to prevent cardiomyopathy, bleb disease in the lung, treat corneal abrasion, treat injured nerves or nerve grafts).

Tissue grafts can be prepared for therapeutic use, in particular, implantation according to the passivation methods disclosed herein. Passivated tissue grafts can include, but are not limited to, grafts of vein, connective tissue, bone, ligament, tendon, skin, and muscle. Passivated tissue grafts also include autologous tissue, extracellular matrix tissue (e.g., collagen or proteoglycan) and tissue substitutes. Tissue substitutes include, but are not limited to, silicone, collagen, fibronectin, glycosaminoglycan, polyurethane, polyvinyl and nylon. Passivated vein grafts are especially desirable, for example, to prevent or reduce stenosis.

The passivated vein graft can then be implanted into an artery to replace or bypass a diseased segment of the artery, such as an area comprising an arterial plaque, thereby preventing or reducing stenosis by reducing intimal hyperplasia. Passivated vein grafts can be implanted according to methods known in the art, including suturing, Anastomotic Coupler and bonding. In some applications, only the exterior surface of the vein graft will be passivated.

Likewise, arteriovenous fistula ("AVF") can be prepared for therapeutic use according to the passivation methods disclosed herein. Passivated AVF can comprise circulatory tissues, e.g., vein, artery, etc. Passivated AVF can also include autologous tissue, extracellular matrix tissue (e.g., collagen or proteoglycan) and tissue substitutes. Tissue substitutes include, but are not limited to, silicone, collagen, fibronectin, glycosaminoglycan, polyurethane, polyvinyl and nylon. Passivated AVF are useful, for example, to increase patency rates in connection with vascular access, e.g., for use in hemodialysis in people with severe kidney disease.

Passivated vascular grafts or passivated AVF are also useful to strengthen any graft or AVF including arterial grafts, for example, to prevent aneurysm. Increasing the strength of the graft prior to implantation facilitates suturing, prevents tearing and in small grafts (e.g., micro-grafts) prevents immediate thrombus. In particular, passivated AVF are useful for vascular access, e.g., in kidney dialysis treatment.

Passivation can also be conducted during the use of interventional radiology, for example, to treat the outside of a vessel at the same time treatment to the inside of the vessel is provided, to therefore allow for more aggressive endovascular treatment.

Passivation of tissue prior to therapeutic use can be conducted according to the methods described here in to prepare improved tissue for therapeutic use. For example, grafts comprising host tissue can be passivated prior to knee and hip replacements or ligament and tendon surgeries.

In certain embodiments, a photoactive agent, e.g., Rose Bengal, can be applied, e.g. by brushing, dripping or spraying onto, or injecting into, tissue surfaces (e.g., a single surface in some cases) of a tissue prior to the application of electromagnetic energy, followed by irradiation at an irradiance of less than about 1 W/cm$^2$. Penetration of topically applied Rose Bengal is about 100 μm or less into connective tissue. Therefore, photoactive dyes such as Rose Bengal can be topically applied to, and/or accumulated within, limited areas of a tissue graft or fistula, such as the external surface of a vein graft or fistula (i.e., the dye does not penetrate into the vessel lumen and in some cases, does not penetrate beyond the external layer of collagen fibers surrounding the vein). Similarly, vein grafts or arteriovenous fistula can be prepared for therapeutic use by providing Rose Bengal to the tissue and irradiating the tissue at an irradiance of less than about 1 W/cm$^2$.

In other embodiments, a chemical cross-linking compound, e.g., EDC or Genepin, can be applied, e.g. by brushing, dripping or spraying onto, or injecting into, tissue surfaces (e.g., a single surface in some cases) of a tissue graft or arteriovenous fistula under conditions sufficient to promote cross-linking of proteins within the graft or arteriovenous fistula surface. In still other embodiments, chemical cross-linking compounds such as EDC and Genepin can be topically applied to, and/or accumulated within, limited areas of a tissue graft or arteriovenous fistula, such as the external surface of a vein graft or arteriovenous fistula (i.e., the compound does not penetrate into the vessel lumen and in some cases, does not penetrate beyond the external layer of collagen fibers surrounding the vein). Likewise, vein grafts can be prepared for implantation by exposing the graft to chemical cross-linking compounds such as, e.g. EDC and Genepin, under conditions sufficient to promote cross-linking of proteins within the grant surface.

EXAMPLES

The invention is additionally described by way of the following illustrative, non-limiting examples that provide a better understanding of the present invention and of its many advantages.

Example 1: Tissue Surface Passivation in a Rabbit Model for Capsular Contraction A pilot experiment in a rabbit model for capsular contraction was developed. Three sub-cutaneous pockets were made by surgical incision on the upper rabbit flank. One pocket was left untreated and surgically closed (No fibrin glue). Of the remaining two, one was treated with Fibrin Glue only, and one received Fibrin Glue+RB (0.1% Rose Bengal)+532 nm light (3 min at 350 mW). Fibrin glue is known to produce a fibrotic reaction in this model. After two weeks all three pockets were surgically re-accessed and inspected. Tissue harvested at two weeks demonstrated an aggressive inflammatory response, with a significant infiltrate within the implant pockets instilled with fibrin glue (FIG. 1). The pockets treated with PTP prior to fibrin glue application, had less infiltrate. These cells also appear contained under layers of presumably, cross-linked collagen. A biodegradation assay was also performed. Pockets were treated as described above at both a low (1 J/cm$^2$) and high (25 J/cm$^2$) fluence. Fluence was measured using FieldMax II laser power meter (Coherent, Santa Clara, Calif.). Immediately following, the skin and fascia were removed. Treated and untreated fascia were biopsied with a six mm punch biopsy, weighed and subjected to digestion in a 1% collagenase (Sigma Aldrich, St. Louis, Mo.) solution at 37° C. Time for complete digestion (the lack of any visible fibers) was recorded for each sample and corrected by weight.

Figure 2:
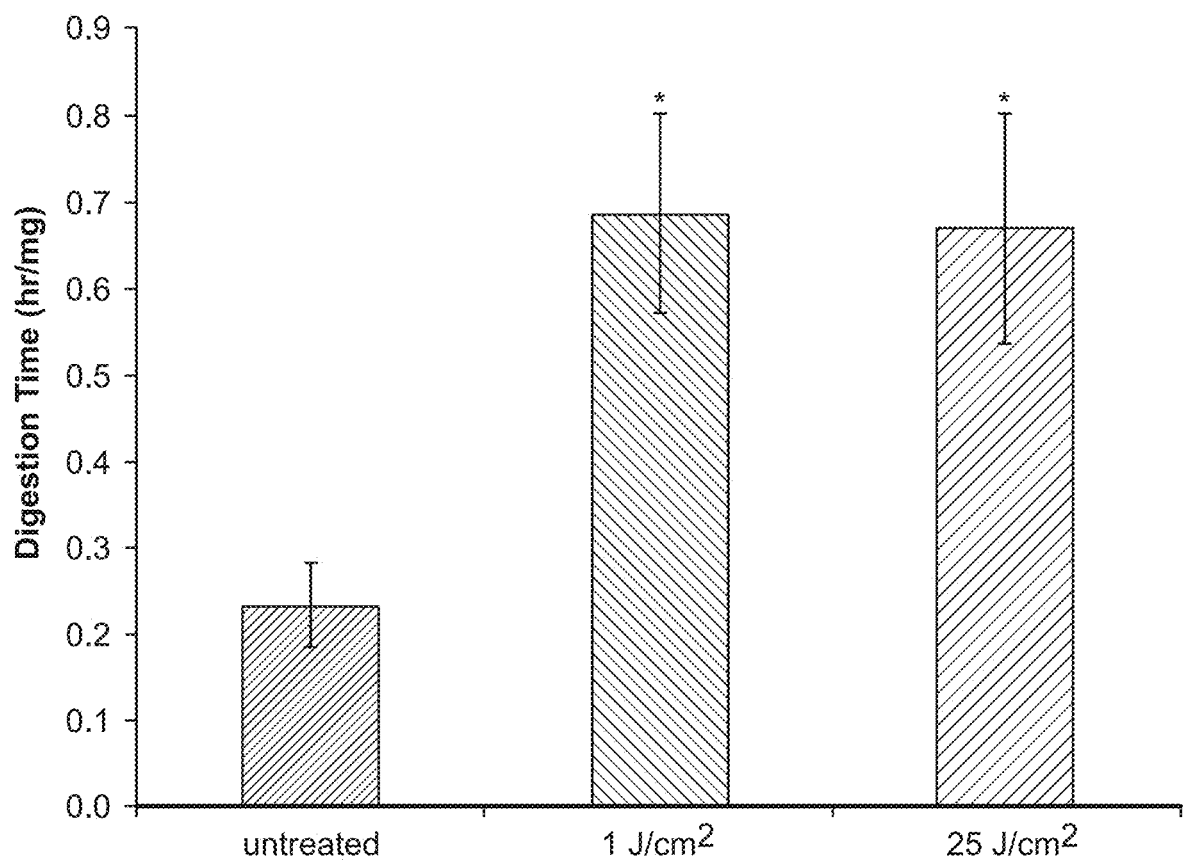
FIG. 2 depicts a graph of digestion times for fascia treated with the PTP. Error bars represent standard deviation. * indicates p<0.005.

In vitro studies confirmed that photochemical tissue passivation, under the conditions that were subsequently used in the animal study, could successfully alter the fascia of the implant pocket. The collagenase digestion assay demonstrated that PTP treatment resulted in a 300% increase in degradation time, which correlates to an increase in collagen cross-linking in fascia when compared to untreated tissue (FIG. 2). Increasing the power of the laser, did not increase collagen cross-linking proving adequate treatment at the lower fluence (1 J/cm$^2$) in this model. Thus, RB+light leads to tissue surface passivation.

Example 2: Tissue Surface Passivation in a Pre-Clinical Model of Capsular Contracture Following Prosthetic Implant Placement The effect of Photochemical Tissue Passivation in a pre-clinical model of capsular contracture following prosthetic implant placement was evaluated. Under general anesthesia, Nine New Zealand white rabbits received three, six cc smooth saline implants placed in the dorsal subpanniculus soft tissue. Each Rabbit received one control implant and two experimental implants.

Briefly, the subpanniculus carnosus plane in the dorsum region was dissected and a single customized six cc saline smooth implant with pressure port valve (Allergan Inc., CA, USA) was placed. A total of three implants were placed on the dorsum of each rabbit. The control group consisted of an implant with no Fibrin Glue and no PTP treatment. Before implant placement, the pocket site of the PTP experimental group was treated with 2 ml 0.1% Rose Bengal in a phosphate buffered saline, and was then exposed to green laser light at 532 nm from a continuous wave KTP laser (Laserscope Aura-I, San Jose, Calif.). The second experimental group consisted of an implant with Fibrin Glue only. Prior to implant placement, all experimental pockets were injected with five cc of fibrin glue, 500|μl of 10% CaCl, 1000 units of thrombin in one milliliter of 50 mM TrisCl as a contracture inducing agent. The incisions were closed in two layers with subdermal 4-0 Vycril and 4-0 interrupted nylon sutures. Topical fibrin glue was applied to the implant pockets in all experimental groups to induce subsequent capsular contracture.

Accordingly, the experimental groups can be summarized as follows:

Group 1: Control group—"Standard Breast Augmentation" ~One pocket per Rabbit undergoing standard implant placement with no Fibrin Glue or Passivation. One six cc smooth saline implant was placed per pocket. The incisions were closed in two layers with subdermal 4-0 Vicryl and 4-0 interrupted nylon sutures.

Group 2: Experimental group—"Fibrin Glue only" ~One dorsal pocket per Rabbit is dissected. Fibrin glue was injected into the implant pocket as a capsular contracture-inducing agent. One six cc smooth saline implants was placed per pocket. The incision was closed as above.

Group 3: Experimental group—"Pre-implant Tissue Passivation" ~One dorsal pocket per Rabbit was dissected. Rose Bengal dye was applied. The pocket was exposed to green laser light at 532 nm from a continuous wave KTP laser (Laserscope Aura-I, San Jose, Calif.). Fibrin glue was injected into the implant pocket as a capsular contracture-inducing agent. Following fibrin glue injection, one six cc smooth saline implant was placed per pocket. The incision was closed as above.

Figure 3:
FIG. 3 depicts smooth muscle actin immunohistochemistry at eight weeks. Tissue from a control pocket that did not receive fibrin glue (left) and tissue from fibrin glue instilled pockets (center and right) is shown. PTP treated pocket is shown on the right. (Scale Bar=100 µm).

Capsule specimens were fixed with 10% buffered formalin and embedded in paraffin. Sections were stained with both Masson Trichrome, and SMA antibody and evaluated histologically and capsular thickness was measured. Smooth muscle actin immunohistochemistry revealed substantial variation in fiber thickness, orientation and number among the various groups. Untreated pockets receiving fibrin glue resulted in multiple layers of SMA within the entire capsule, hundreds of microns from the implant. Treated pockets exhibited significantly less deposition of smooth muscle actin. In fact, the SMA pattern in capsules harvested from the treated groups resembled those, which had not been instilled with fibrin glue (FIG. 3).

Figure 4:
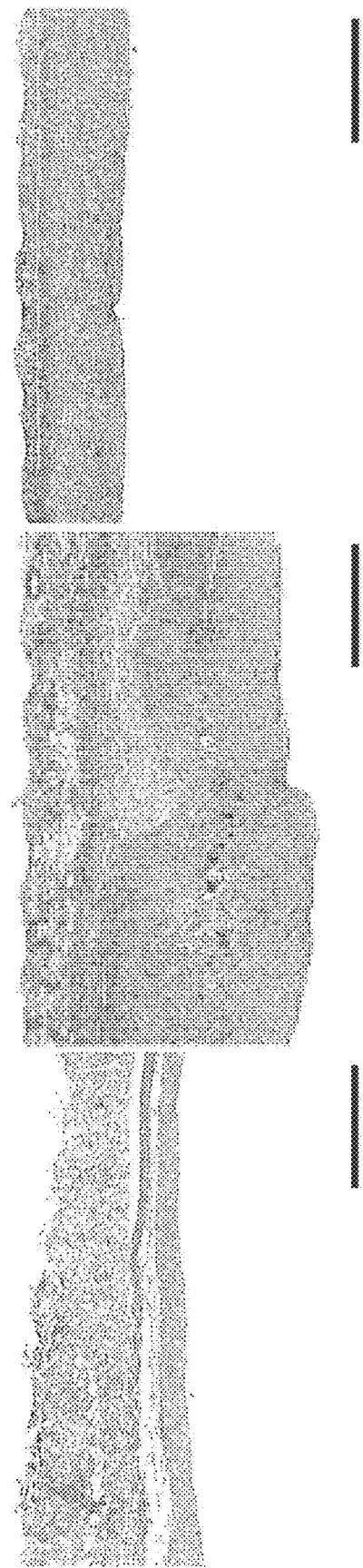
FIG. 4 depicts the results of three sub-cutaneous pockets made by surgical incision on the upper rabbit flank in a rabbit model for capsular contracture. Capsule tissue stained with mason's trichrome at eight weeks. Tissue from a control pocket that did not receive fibrin glue (left), tissue from a fibrin glue instilled pockets (center and right). PTP treated pocket on the right (Scale Bar=500 µm). In this model Fibrin Glue is used to induce capsular contracture. Histology shows a significant decrease in capsular thickness in the Fibrin Glue+Photochemical Tissue Passivation group compared to Fibrin Glue alone control. The Fibrin Glue+Photochemical Tissue Passivation group had similar capsule thickness to the healthy, normal, no Fibrin Glue control.
Figure 5:
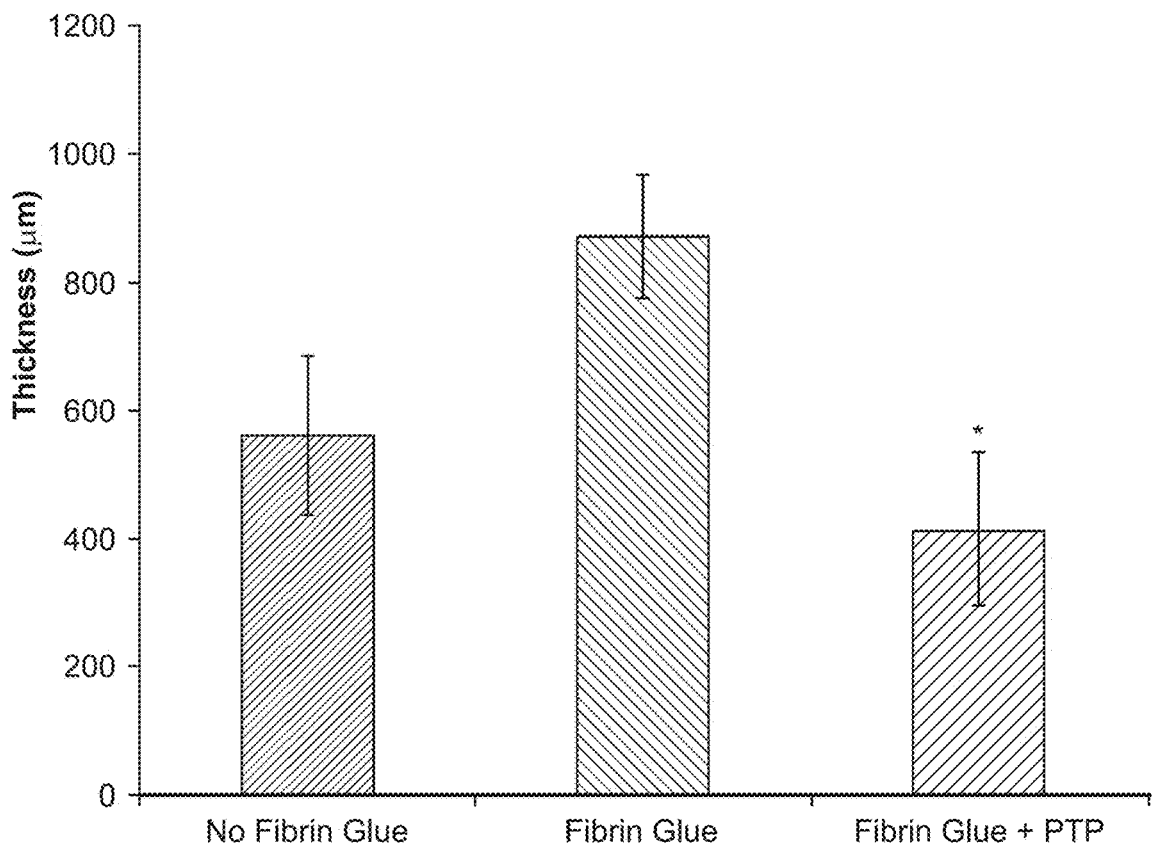
FIG. 5 depicts a graph of capsule thickness at eight weeks in a rabbit model.

Histology shows a decrease in capsular thickness in the Fibrin Glue+Photochemical Tissue Passivation group compared to Fibrin Glue alone control. The Fibrin Glue+Photochemical Tissue Passivation group had similar capsule thickness to the healthy, normal, no Fibrin Glue control (FIG. 4). The passivated group had a 52% decrease in capsule thickness when compared to the controls (FIG. 5).

Implant capsule thickness is the number one prognostic factor for contracture development. The treated pockets also demonstrated decreased inflammation and vascularity within the capsule. PTP resulted in a less fibrohistiocystic cells, macrophages and synovial metaplasia. Accordingly, use of Rose Bengal+Light in tissue passivation preserved normal tissue architecture and prevented the development of pathogenic collagen bundles and capsular contracture.

Example 3: Photochemical Tissue Passivation for Prevention of Vein Graft Intimal Hyperplasia Vein grafts are frequently used for Coronary Artery Bypass Grafting yet suffer poor long-term patency rates compared to arterial grafts due to accelerated atherosclerosis. This begins as intimal hyperplasia (IH), which is a consequence of intimal injury resulting from surgical trauma and excessive dilation of the vein graft as it is exposed to arterial pressures. Limiting this stretch reduces the degree of IH. To date, this has only been achieved with external sheaths. Photochemical Tissue Passivation (PTP) was conducted to determine whether this procedure could improve the long-term patency rates of venous grafts.

Porcine jugular veins were used to evaluate the effect of PTP on the elasticity of venous tissues. Veins harvested from five pigs were divided in half. One segment served as control, the other was treated (PTP) with 0.1% Rose Bengal and a 532 nm laser (delivering 25 $J/cm^2$). Veins were cut into 0.5×2 cm strips (N=33; 16 control, 17 treated). Stress-strain curves were generated for each with a tensiometer and the modulus of elasticity calculated.

Figure 6:
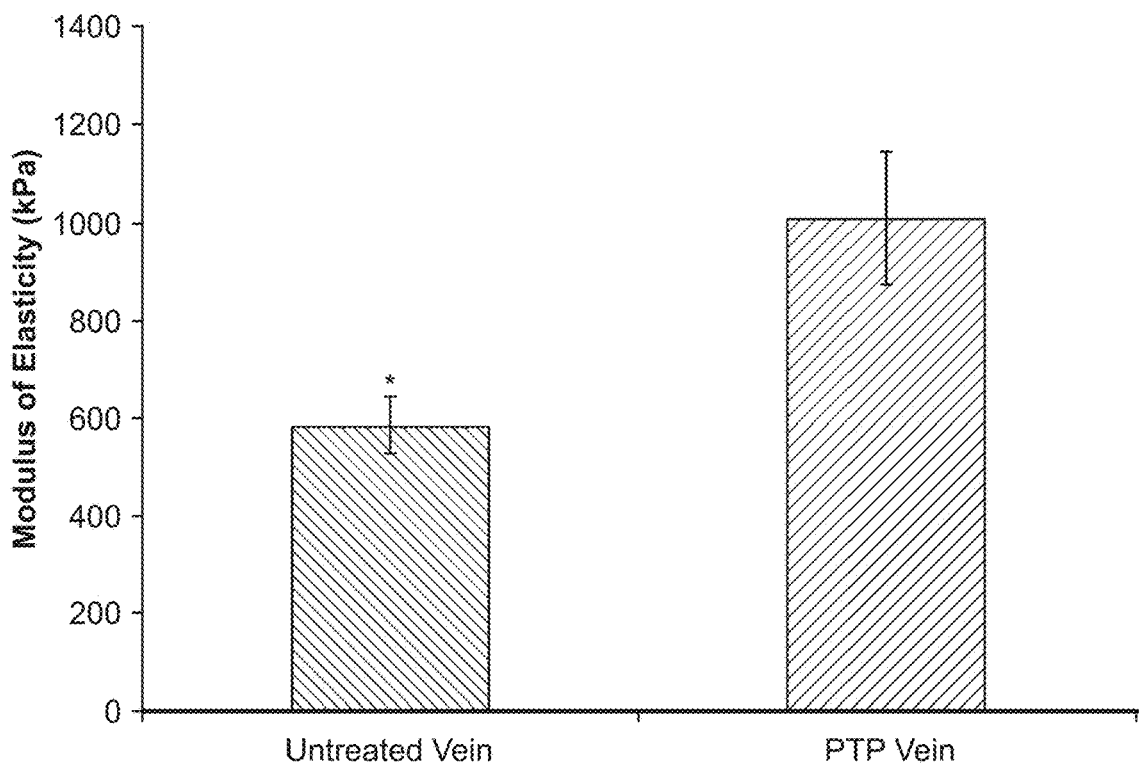
FIG. 6 depicts a graph of the modulus of elasticity (Young's modulus) of untreated vein grafts, and treated vein grafts. Error bars represent standard deviation. * indicates p=0.01.

The modulus of elasticity (Young's modulus) of treated and untreated veins were 1008+555 and 587+228 KPa respectively (p=0.01). The modulus of elasticity of venous grafts was increased 2-fold via PTP (FIG. 6). The Young's modulus of arterial samples (N=12) was 1515+530 KPa.

TABLE 1

Modulus of elasticity (Young's modulus) of untreated veins, treated veins, and artery

| | Young's Modulus (KPa) | P value |
|---|---|---|
| Untreated porcine jugular vein (N = 16) | 587 + 288 | 0.01 |
| Treated porcine jugular vein - 25 $J/cm^2$ (N = 17) | 1008 + 555 | |
| Porcine carotid artery (N = 12) | 1515 + 530 | |

A biodegradation assay was performed to demonstrate collagen cross-linking. Collagenase digestion experiments were conducted using segments of superficial epigastric vein harvested from Sprague-Dawley rats, which was the same conduit used for the animal model. A single vein was harvested from two rats under an operating microscope using a strict "no touch" technique. Each vein was divided in four equally long segments, resulting in eight total samples. Half of the samples were treated with PTP, delivering 25 $J/cm^2$ as described above. Half served as controls. The samples were immersed in 0.1% (w/v) collagenase solution and placed in an incubator at 37° C. Time to complete digestion was measured.

Figure 7:
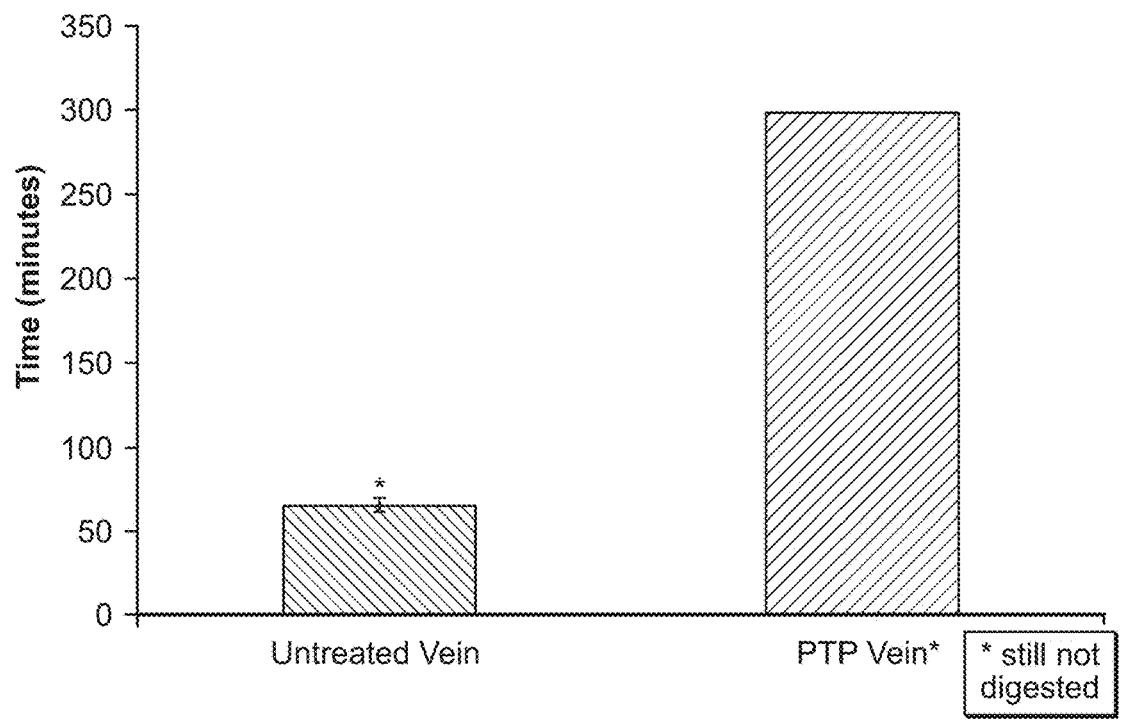
FIG. 7 depicts a graph of collagen digestion times for untreated and treated vein grafts. * indicates p<0.001.

Collagenase assays demonstrate significant collagen cross-linking of venous grafts after PTP (FIG. 7). Collagenase digestion of controls was achieved in 66 minutes on average, while treated veins were undigested after 300 minutes.

In vivo testing was done by placing a reversed epigastric vein interposition graft in the femoral artery of Sprague-Dawley rats. Grafts were harvested after four weeks. A total of 16 rats underwent a femoral interposition graft with reversed epigastric vein. Half of the vein grafts (N=8) were treated with PTP using 25 J/cm$^2$ of fluence. Average operative time was two hours. Additional operative time for PTP was 4-5 minutes on average. There were three instances of surgical wound dehiscence between post-operative day one and two; one in the control group and two in the experimental group. These wounds were irrigated and resutured. None of the grafts were exposed. There were no wound infections. After four weeks, 100% of the vein grafts were patent. There were no pseudoaneurysms or aneurysmal dilatation of the grafts. Histologic cross-sections of the mid-portion of the graft were analyzed using light microscopy. Intimal thickness was measured as the distance between the internal elastic lamina and the vessel lumen. These in-vivo studies revealed neointimal thickness of 80+56 and 24+22 μm for untreated (N=8) vs. treated animals respectively (N=8).

TABLE 2

Intimal thickness of untreated and treated vein grafts after four weeks

|  | Intimal Thickness (um) | P value |
| --- | --- | --- |
| Untreated vein grafts (N = 8) | 80 + 56 | 0.03 |
| Treated vein grafts (N = 8) | 24 + 22 |  |

There was also marked reduction in smooth muscle hypertrophy and medial thickness in the treated compared to the untreated grafts. Medial thickness in untreated grafts was 216+69 um compared to 141+40 μm in treated grafts (p=0.04).

TABLE 3

Medial thickness of untreated and treated vein grafts after four weeks

|  | Medial Thickness (um) | P value |
| --- | --- | --- |
| Untreated vein grafts (N = 8) | 216 + 69 | 0.04 |
| Treated vein grafts (N = 8) | 141 + 40 |  |

Figure 8A:
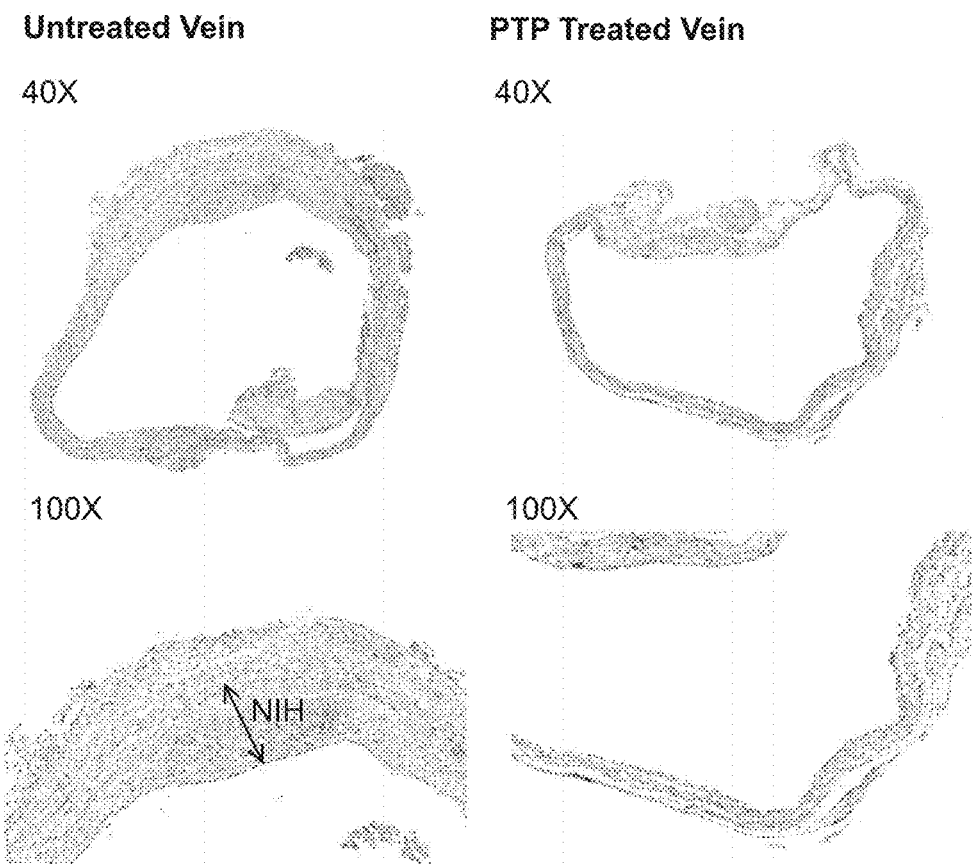
FIG. 8A depicts a histologic cross-section of venous grafts four weeks following implantation. Slides were prepared with Van-Gieson elastin stain.
Figure 8B:
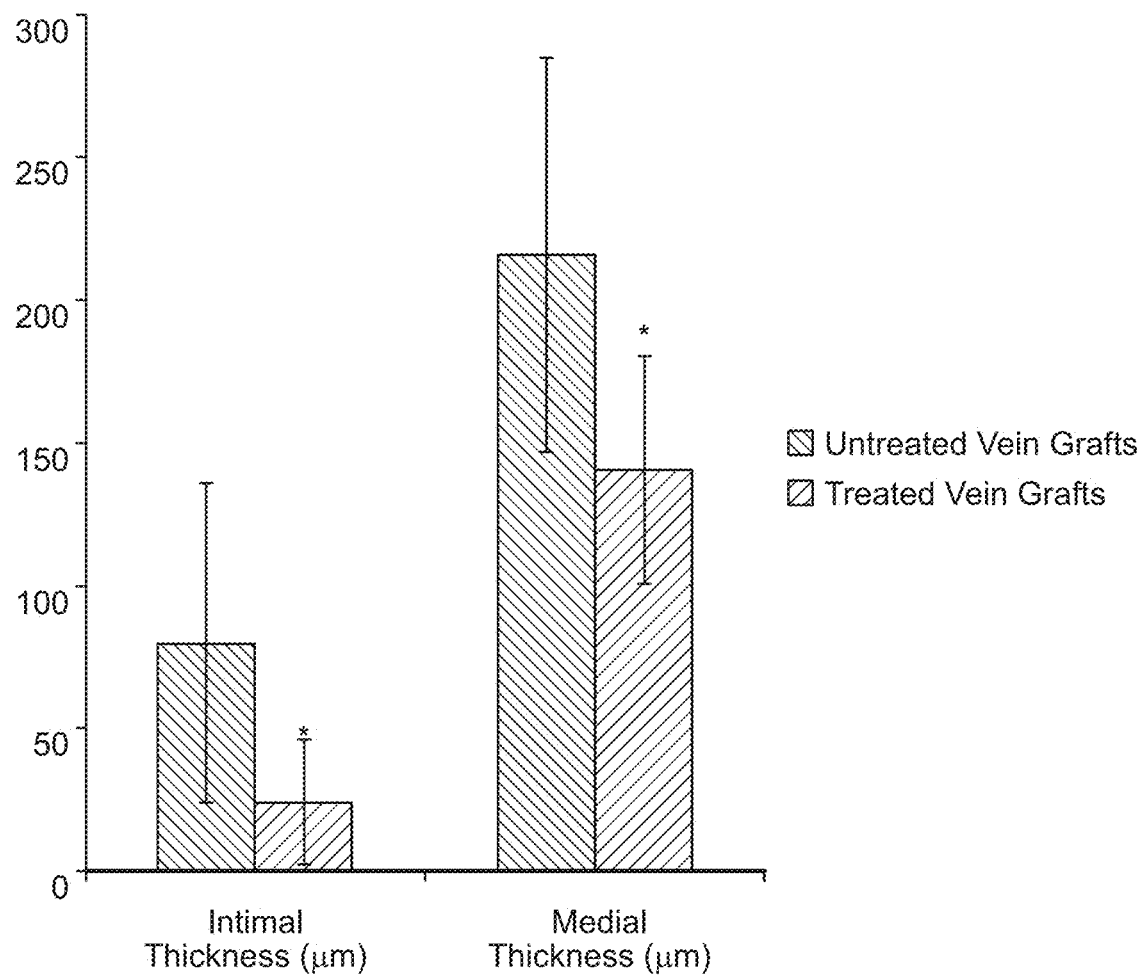
FIG. 8B depicts a graph comparing medial and intimal thickness of untreated vs. treated grafts. Error bars represent standard deviation. * indicates p=0.03 & p=0.04, respectively.
Figure 9:
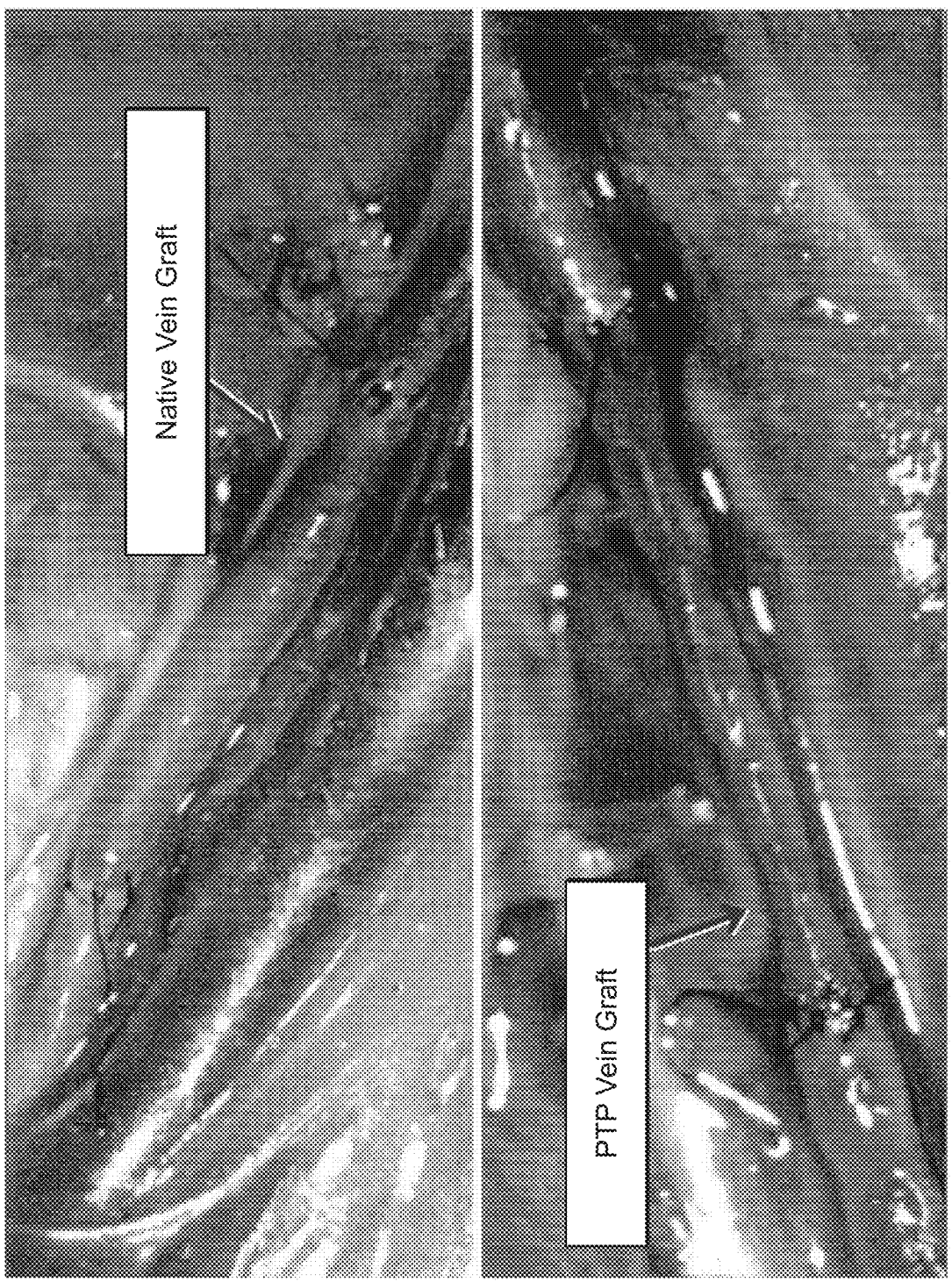
FIG. 9 depicts images of venous grafts both untreated (top) and PTP treated (bottom) after clamp removal and restoration of blood flow. Images show varying degrees of graft distention between groups.

The animal model demonstrated a 70% reduction in neointimal thickness of treated grafts (FIGS. 8A and 8B). Images of vein grafts after vessel clamp removal (i.e., with restored blood flow to the graft) shows less distention in PTP treated vein grafts compared to untreated controls (FIG. 9).

Therefore, PTP improves the long-term patency rates of venous grafts used for coronary revascularization, peripheral arterial disease and arteriovenous fistula for vascular access without the use of cumbersome external sheaths.

Example 4: Chemical Cross-Linking Passivation for Prevention of Vein Graft Intimal Hyperplasia Saphenous veins and carotid arteries were harvested from Yorkshire pigs and flushed with heparinized saline. Saphenous veins were either treated with the chemical cross-linker 1-ethyl-3-(3-dimethylaminopropyl)-carbodiimide ("EDC"), the photo cross-linker Rose Bengal and green light (PTP) or left untreated.

Figure 10A:
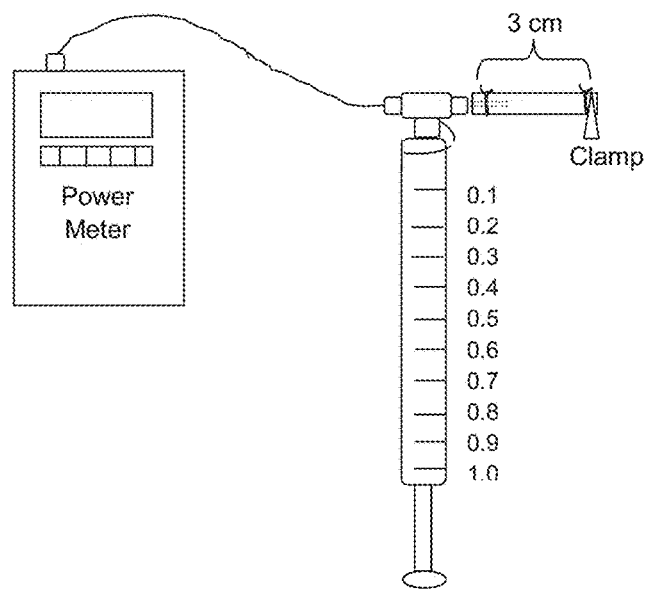
FIG. 10A depicts a system to measure vessel compliance, including a pressure transducer and a syringe connected to the pressure transducer via a three-way stopcock.
Figure 10B:
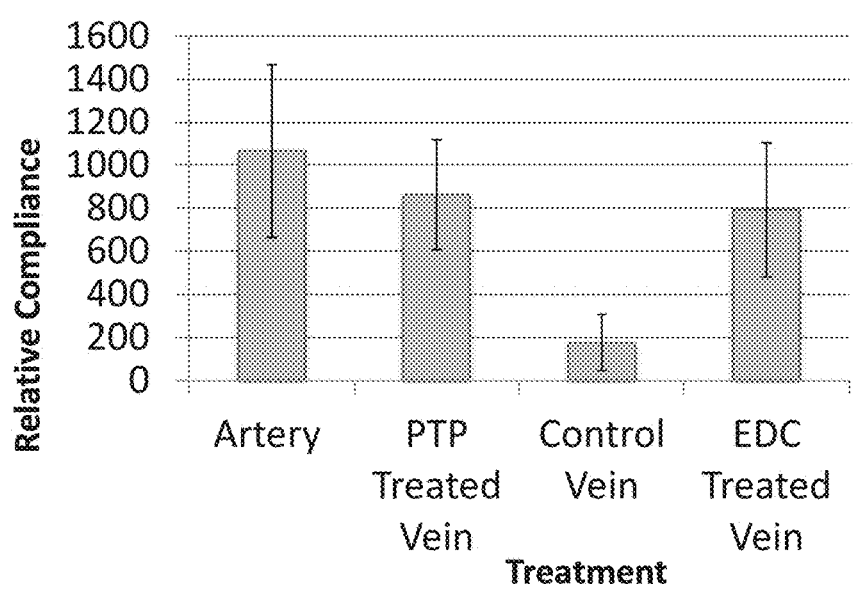
FIG. 10B depicts compliance curves generated for each specimen (artery, PTP treated vein, untreated vein (control)) and EDC treated vein and the relative compliance calculated as the slope of the curve pertaining to physiologic pressure.

A pressure transducer (FIG. 10A) was used to measure vessel compliance. The vessels were cut into 3 cm-long sections. The distal ends of the vein segments were marked with a marking pen to maintain proper orientation of venous valves. The vessels were intubated with a 24-gauge angio-catheter tip and secured with a silk tie. The distal end of the specimen was also tied off with a silk suture and clamped. Through a 1 ml syringe connected to the pressure transducer via a three-way stop-cock (FIG. 10A), 1 ml of normal saline was instilled into the vessel in 0.1 ml-increments, and the corresponding pressure values were recorded. Compliance curves (FIG. 10B) were generated for each specimen and the relative compliance was calculated as the slope of the curve pertaining to physiologic pressure.

TABLE 4

Mean and Standard Deviation

|  | Artery | Control Vein | EDC Treated Vein | PTP Treated Vein |
| --- | --- | --- | --- | --- |
| Mean | 1066 | 176 | 792 | 863 |
| STDEV | 402 | 130 | 311 | 255 |

The compliance of artery, PTP treated vein and EDC treated vein were significantly different from untreated control vein. There was no significant difference among artery, PTP treated vein and EDC treated vein. Analysis of Variance (One-Way) was performed to determine significance. Significance was set at a 95% confidence interval, p<0.05 was considered statistically significant. Data analysis was performed using StatPlus statistical software (AnalystSoft, Inc., Vancouver, British Columbia, Canada).

Figure 11A:
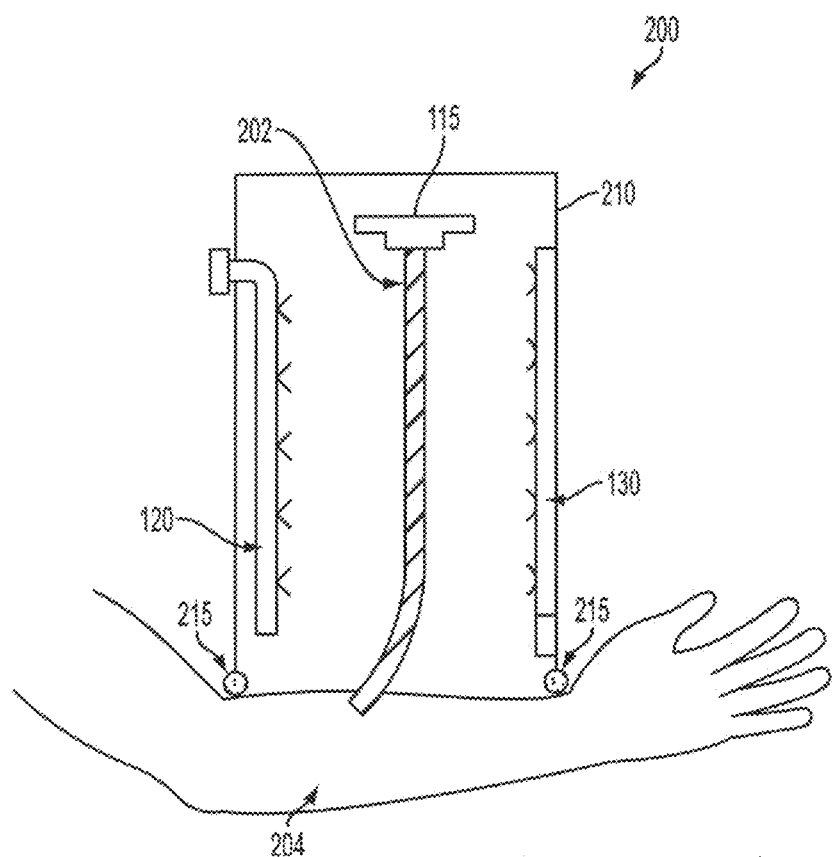
FIG. 11A depicts an apparatus for treating a vein segment used to form an arteriovenous fistula according to an embodiment of the invention.

Example 5: Preparation of an Arteriovenous Fistula (AVF) in a Patient Requiring Hemodialysis In order to facilitate vascular access in a patient requiring hemodialysis treatments, a vein in the arm of the patent can be joined directly to a nearby artery through an anastomosis to create an arteriovenous fistula. With reference to FIG. 11A, the apparatus 200 can be used to apply a TSSA to a vein segment 202 of the patient that will form an arteriovenous fistula, thereby passivating the vein segment to improve the strength and patency of the vein segment.

A vein segment 202 that will form the fistula can be separated from the arm 204 and affixed to the clamp 115 within the housing 110. The lower portion of the housing 210 of the apparatus 200 can be at least partially open, to allow the severed end of the vein segment 202 to be directed into the interior of the housing 210 and affixed to a vein clamp 115. A lower clamp, spacer, or the like can be provided to stabilize the lower end of the vein segment 202 where it enters the apparatus 200. The bottom of the housing 210 can be shaped to contact the arm 204 of the patient. A seal 215 (e.g., a flexible material) can be provided on the lower edges of the housing 210 to improve contact of the housing 210 with the arm 204, e.g., to help enclose the interior volume of the housing 210 during the procedure.

The apparatus 200 includes one or more applicator arrangements 120 and light-emitting arrangements 130, which can be provided with a variety of components and configurations. For clarity, exemplary details of these arrangements are not shown in FIG. 11A. A humidifying arrangement can also be provided to maintain a hydrated environment for the vein segment 202 during treatment.

The apparatus 200 can be used to apply a passivation agent to the vein segment 202, as described above, and, in the case of a photoactive agent, the vein segment 202 can then be irradiated using light-emitting arrangement 130. The lower portion of the housing 210 can optionally be structured to catch excess TSSA and/or prevent it from entering the incision created in the arm 204 to extract the vein segment 202.

The total time for this in situ treatment process can be on the order of a few minutes or more, and may thus be sufficiently brief so as not to present a significant interruption of the fistula procedure. The crosslinking prevents tissue expansion in all directions. The decrease in vessel dilitation reduces intimal injury, intimal hyperplasia and subsequent stenosis. Cross-linking also limits lengthening and subsequent vessel tortuousity thus preventing turbulent flow which also leads to stenosis/thrombosis.

Figure 11B:
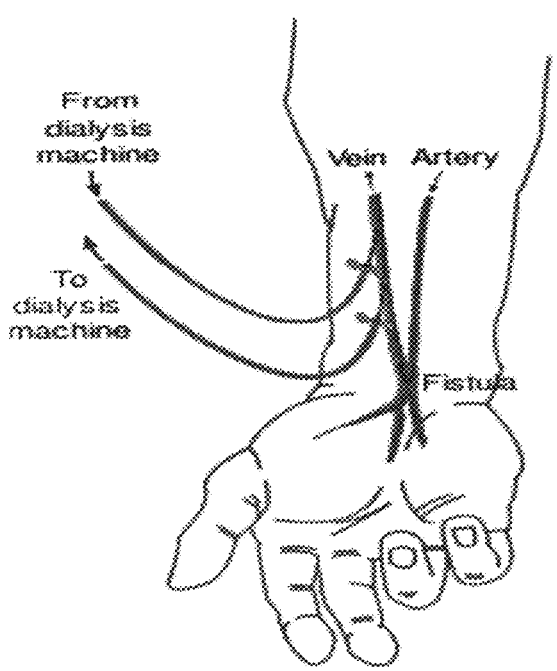
FIG. 11B depicts attachment of a dialysis machine following formation of the fistula.

Following treatment with the TSSA, the apparatus 200 can be removed, and the strengthened vein segment 202 is then connected to the artery creating the fistula. Upon formation of the fistula, a dialysis machine can then be connected to the vein as shown in FIG. 11B.

REFERENCES

1. Cunningham B, McCue J. Safety and effectiveness of Mentor's MemoryGel implants at 6 years. Aesthetic Plast Surg. 2009; 33:440-4.
2. Adams W P, Jr., Haydon M S, Raniere J, Jr., et al. A rabbit model for capsular contracture: development and clinical implications. Plast Reconstr Surg. 2006; 117:1214-9; discussion 20-1.
3. Adams W P, Jr. Capsular contracture: what is it? What causes it? How can it be prevented and managed? Clin Plast Surg. 2009; 36:119-26, vii.
4. Young V L. Guidelines and indications for breast implant capsulectomy. Plast Reconstr Surg. 1998; 102:884-91; discussion 92-4.
5. Dancey A, Nassimizadeh A, Levick P. Capsular contracture—What are the risk factors?—A 14 year series of 1400 consecutive augmentations. J Plast Reconstr Aesthet Surg. 2011.
6. Spear S L, Low M, Ducic I. Revision augmentation mastopexy: indications, operations, and outcomes. Ann Plast Surg. 2003; 51:540-6.
7. Pajkos A, Deva A K, Vickery K, Cope C, Chang L, Cossart Y E. Detection of subclinical infection in significant breast implant capsules. Plast Reconstr Surg. 2003; 111:1605-11.
8. Chen N T, Butler P E, Hooper D C, May J W, Jr. Bacterial growth in saline implants: in vitro and in vivo studies. Ann Plast Surg. 1996; 36:337-41.
9. Virden C P, Dobke M K, Stein P, Parsons C L, Frank D H. Subclinical infection of the silicone breast implant surface as a possible cause of capsular contracture. Aesthetic Plast. Surg. 1992; 16:173-9.
10. Kamel M, Protzner K, Fornasier V, Peters W, Smith D, Ibanez D. The peri-implant breast capsule: an immunophenotypic study of capsules taken at explantation surgery. J Biomed Mater Res. 2001; 58:88-96.
11. Mazaheri M K, Schultz G S, Blalock T D, Caffee H H, Chin G A. Role of connective tissue growth factor in breast implant elastomer capsular formation. Ann Plast Surg. 2003; 50:263-8; discussion 8.
12. Domanskis E, Owsley J Q, Jr. Histological investigation of the etiology of capsule contracture following augmentation mammaplasty. Plast Reconstr Surg. 1976; 58:689-93.
13. Tamboto H, Vickery K, Deva A K. Subclinical (biofilm) infection causes capsular contracture in a porcine model following augmentation mammaplasty. Plast Reconstr Surg. 2010; 126:835-42.
14. Katzel E B, Koltz P F, Tierney R, et al. A novel animal model for studying silicone gel-related capsular contracture. Plast Reconstr Surg. 2010; 126:1483-91.
15. Johnson T S, O'Neill A C, Motarjem P M, et al. Photochemical tissue bonding: a promising technique for peripheral nerve repair. J Surg Res. 2007; 143:224-9.
16. Yao M, Yaroslaysky A, Henry F P, Redmond R W, Kochevar I E. Phototoxicity is not associated with photochemical tissue bonding of skin. Lasers Surg Med. 2010; 42:123-31.
17. Kamegaya Y, Farinelli W A, Vila Echague A V, et al. Evaluation of photochemical tissue bonding for closure of skin incisions and excisions. Lasers Surg Med. 2005; 37:264-70.
18. Wang Y, Kochevar I E, Redmond R W, Yao M. A light-activated method for repair of corneal surface defects. Lasers Surg Med. 2011; 43:481-9.
19. Chan B P, Kochevar I E, Redmond R W. Enhancement of porcine skin graft adherence using a light-activated process. J Surg Res. 2002; 108:77-84.
20. Ibusuki S, Halbesma G J, Randolph M A, Redmond R W, Kochevar I E, Gill T J.
Photochemically cross-linked collagen gels as three-dimensional scaffolds for tissue engineering. Tissue Eng. 2007; 13:1995-2001.
21. Baker J J L, inventor Augmentation mammaplasty. Symposium on aesthetic surgery of the breast. 1978

EQUIVALENTS

From the foregoing description, it will be apparent that variations and modifications may be made to the invention described herein to adopt it to various usages and conditions. Such embodiments are also within the scope of the following claims.

INCORPORATION BY REFERENCE

All patents, patent applications and publications mentioned in this specification are herein incorporated by reference to the same extent as if each independent patent and publication was specifically and individually indicated to be incorporated by reference.

The invention claimed is:

1. A method of preventing or reducing stenosis in a subject, the method comprising implanting a passivated graft comprising vein into an artery, wherein the implanting of the graft replaces and/or bypasses a diseased segment of the artery and wherein the passivated graft comprising vein is prepared by exposing the exterior surface of the passivated graft comprising vein to a tissue structure stabilizing agent ("TSSA") under conditions sufficient to promote cross-linking of proteins within the exterior surface of the vein while preserving normal tissue architecture of regions of the passivated graft comprising vein beyond the external layer of collagen, thereby preventing or reducing stenosis in a subject.

2. The method of claim 1, wherein the TSSA is a photoactive agent or a chemical cross-linking compound.

3. The method of claim 1, wherein the TSSA is a photoactive agent.

4. The method of claim 3, wherein the photoactive agent is Rose Bengal ("RB").

5. The method of claim 4, wherein the TSSA does not penetrate more than about 100 μm into connective tissue.

6. The method of claim 3, wherein the photoactive agent is selected from the group consisting of xanthenes, flavins, thiazines, porphyrins, expanded porphyrins, chlorophylls, phenothiazines, cyanines, mono azo dyes, azine mono azo dyes, rhodamine dyes, benzophenoxazine dyes, oxazines, and anthroquinone dyes.

7. The method of claim 3, wherein the photoactive agent is selected from the group consisting of Rose Bengal ("RB"), erythrosine, riboflavin, methylene blue (MB), Toluidine Blue, Methyl Red, Janus Green B, Rhodamine B base, Nile Blue A, Nile Red, Celestine Blue, Remazol Brilliant Blue R, riboflavin-5-phosphate (R-5-P), N-hydroxypyridine-2-(I H)-thione (N-HTP) and photoactive derivatives thereof.

* * * * *